United States Patent [19]

Brigati

[11] Patent Number: 5,116,727
[45] Date of Patent: May 26, 1992

[54] HYBRIDIZATION METHOD AND COMPOSITION WITH ALTERNATING POLYSACCHARIDE OF SULFATED N-ACETYLGALACTOSAMINE

[75] Inventor: David J. Brigati, Edmond, Okla.

[73] Assignee: Iniziative Marittime 1991, S.r.L., Turin, Italy

[21] Appl. No.: 404,990

[22] Filed: Aug. 31, 1989

[51] Int. Cl.⁵ .............................................. C12Q 1/68
[52] U.S. Cl. ................................ 435/6; 435/172.3; 436/501; 536/18.7; 536/21; 935/78
[58] Field of Search ................... 435/6, 172.3, 4; 436/501; 935/78; 536/18.7, 21

[56] References Cited

U.S. PATENT DOCUMENTS

| | | |
|---|---|---|
| 4,689,294 | 8/1987 | Bogulawski et al. ............... 435/6 |
| 4,731,335 | 3/1988 | Brigati ............................. 436/180 |
| 4,766,064 | 8/1988 | Williams et al. ................... 435/6 |
| 4,769,319 | 9/1988 | Ellis et al. .......................... 435/6 |

OTHER PUBLICATIONS

K. T. Montone et al. "Detection of Epstein-Barr Virus Genomes . . . " Modern Pathology, vol. 3, No. 1, pp. 89-96 (1990).

A. I. Caplan. "Cartilage", Scientific American, vol. 251 (4) pp. 84-94 (1984).

J. H. Lin et al. "An oligonucleotide probe for the detection . . . " J. of Virol. Meth. vol. 15, pp. 139-149 (1987).

A. White et al. Principles of Biochemistry, pp. 53-54 (4th ed. 1968).

K. T. Montone et al. "Anatomic Viral Detection Is Automated" Yale J of Biol. & Med., vol. 62, pp. 141-158 (1989).

Primary Examiner—Amelia Burgess Yarbrough
Attorney, Agent, or Firm—Pennie & Edmonds

[57] ABSTRACT

Probe cocktails contain a nucleic acid probe and a sulfated polysaccharide as a volume excluding polymer to speed up hybridization rates. Exemplary sulfated polysaccharides are chondroitin sulfate A and C, which can be extracted from cartilage and similar tissues. Compared to synthetic anionic polymers such as dextran sulfate, the probe cocktails can have reduced viscosities and surface tensions, as well as reduced water loss when the cocktail is heated to denature DNA before rehybridization. The reduced viscosity and surface tension are of particular value when entering and exiting narrow spaces, as in some automated analyzers and in capillary gap methodologies.

14 Claims, No Drawings

HYBRIDIZATION METHOD AND COMPOSITION WITH ALTERNATING POLYSACCHARIDE OF SULFATED N-ACETYLGALACTOSAMINE

The present invention relates to methods and compositions for hybridizing nucleic acids such as DNA or RNA for diagnostic or other purposes, and especially to the use of sulfated polysaccharides to facilitate such hybridizations.

Hybridization assays of a number of geometrical arrangements are known. One common feature is that one nucleic acid strand, known as the probe, contains a sequence substantially complementary to the sequence to be detected in the target strand. In virtually all geometries, whether the probe and target are both in solution at the time of their contact with each other or one is immobilized, and whether the probe is labeled or not, the rate of that hybridization step has an appreciable effect upon the speed of the assay. Improving the rate of such hybridization step may also enhance the selectivity or other aspects of the assay. In some assay geometries there are other hybridization steps, e.g., of a second probe to target in sandwich assays, which can also be enhanced.

Such hybridization steps have been enhanced by the use of water soluble polymers, and especially of anionic and non-ionic water soluble polymers having volume excluding properties in aqueous media. Poly(ethylene glycol) is exemplary of the non-ionic polymers that have been used (see U.S. Pat. No. 4,766,064 to Williams et al). The most commonly-used polymer, however, has been dextran sulfate, which is a synthetic product a chemically sulfating a naturally-derived homopolysaccharide of glucose. See also U.S. Pat. No. 4,689,294 of Bogulawski et al disclosing the use of certain synthetic anionic poylacrylate and polymethacrylate polymers.

Heparin is a known naturally occuring heteropolysaccharide used as an anti-coagulant. Heparin contains alternating D-glucouronic acid and D-glucosamine moieties with a high degree of sulfate modification. Most of the glucouronic acid moieties bear sulfate at the 2-carbon. The nitrogen of each D-glucosamine is predominantly also sulfated, although some of the nitrogens may be acetylated, especially in the variant known as heparan sulfate or heparatin sulfate. See A. White et al, Priniciples Of Biochemistry, pages 53-54. Proposals have been made to employ heparin sulfate instead of dextran sulfate in certain hybridization assays. See J. H. Lin et al, "An oligonucleoxide probe for the detection of hepatitis B virus DNA in serum", *J. of Virological Methods*, vol. 15, pp. 139-149 (1987). The present applicant has found, however, that heparin sulfate is a poor choice, because it has low ion-exclusion properties and it loses water volume as the temperature increases to typical denaturation (70-110 deg. C.) and rehybridization (37-80 deg C.) temperatures.

In addition to the assay geometry (e.g., immobilized sample, solution sandwich assay, displacement assay in solution, in situ assay) there are also differences in the macroscopic geometry. Assays may occur within an agitated tube, on a nitrocellulose surface, in a packed column or in the capillary gap environment of U.S. Pat. No. 4,731,335 of Brigati. In many of these macroscopic geometries, and especially the capillary gap environment, excessive solution viscosities or surface tensions should be avoided. Unfortunately, many volume exclusion polymers such as dextran sulfate cause increasing viscosities and surface tensions at increasing concentrations. This increased viscosity inhibits the probe from entering and exiting from small narrow spaces such as microcentrifuge tubes, pipette tips and plastic conduction lines, as employed in various analyzers, and such as capillary action gaps.

BRIEF DESCRIPTION OF THE INVENTION

It has been found that the alternating heteropolysaccharides of sulfonated N-acetylgalactosamine (or SNAGA) can enhance hybridization rates in aqueous media without causing excessive viscosity or surface tension.

Accordingly, the present invention includes a method for increasing the rate of hybridization between two complementary polynucleotide segments in an aqueous medium which comprises the step of forming an aqueous medium containing the two complementary polynucleotide segments and a water-soluble heteropolysaccharide having an alternating structure of sulfated N-acetylgalactosamine and an unsulfated monosaccharide, the water-soluble heteropolysaccharide being of sufficient molecular weight and concentration to produce an observable increase in the rate of hybridization.

One of the two complementary polynucleotide segments can be a target sequence in nucleic acid being analyzed in a sample. The other of the two complementary polynucleotide segments can be a reagent strand, which can be short (oligonucleotide) or long, and can be single-stranded (and can be DNA or RNA) or, at least initially, double-stranded.

The present invention also includes a reagent system for determining a particular polynucleotide segment in a test sample, comprising in the same or different containers in a packaged combination:

a) a polynucleotide probe having a base sequence substantially complementary to the sequence to be determined, and b) a water-soluble heteropolysaccharide having an alternating structure of sulfated N-acetylgalactosamine and an, unsulfated monosaccharide, the water-soluble heteropolysaccharide being of sufficient molecular weight and amount to produce an observable increase in the rate of hybridization when the polynucleotide probe and water-soluble heteropolysaccharide are combined with a sample in an aqueous medium.

DETAILED DESCRIPTION OF THE INVENTION

The water-soluble heteropolysaccharides used in the present invention can be linear or branched, and contain at least a major proportion of their sugar content as an alternating structure of monosaccharides. As discussed more fully below in connection with exemplary heteropolysaccharides taken from cartilage, one of the alternating monosaccharides is sulfated N-acetylgalactosamine, herafter abbreviated as SNAGA. The sulfate is generally attached to the 4-carbon or the 6-carbon of the galactosamine ring. The nitrogen (on the 2-carbon) is acetylated, in contrast with heparin structures wherein the nitrogen is predominantly or exclusively sulfated. The SNAGA residue is generally linked to the other residue with which it alternates by linkages at the 1-carbon and 3-carbon of the galactosamine ring.

Alternating with SNAGA in the heteropolysaccharide is the residue of a non-sulfated sugar such as D-glucuronic acid, L-iduronic acid or D-galactose. These residues impart less anionic character than the SNAGA residues. D-glucuronic acid alternates with SNAGA in the anionic polymers chondroitin sulfate A and chondroitin sulfate C, which can be derived from cartilage. As described in the literature, the sulfate in chondroitin sulfate A is predominantly or exclusively on the 4-carbon of the glucosamine ring, and in chondroitin sulfate C is predominantly or exclusively on the 6-carbon of the glucosamine ring. In another heteropolysaccharide that can be derived from cartilage, keratan sulfate or keratosulfate, D-galactose alternates with SNAGA bearing sulfate predominantly or exclusive on the 6-carbon of the galactosamine ring. Dermatan sulfate or chondroitin sulfate B contains L-iduronic acid alternating with SNAGA having sulfate predominantly or exclusively on the 4-carbon of the galactosamine ring.

It is preferred to use heteropolysaccharides derived from natural sources such as cartilage by mild treatments such as aqueous extraction. In cartilage, it is known that both chondroitin sulfates and keratan sulfates are linked to proteins in complex structures. Generally, the alternating polysaccharide structure, whether linear or branched, is linked by a specific oligosaccharide chain to a specific amino acid. For example, one common structure is:

wherein Ser is a serine residue in the protein, Xyl is xylose, Gal is galactose and GluA is glucuronic acid. See A. I. Caplan, "Cartilage" Scientific American vol. 251(4) pp. 84-94 (1984). Depending upon the type of mild treatment employed, such structure might be cleaved from the protein at the serine-xylose linkage or elsewhere. Furthermore, branch points in the alternating SNAGA-GluA region may be left intact or cleaved in varying degrees.

The molecular weight of the heteropolysaccharide is in generally a function of the average number of repeating disaccharide units (e.g., n in the above structure). For most naturally derived heteropolysaccharides used in the present invention, that average number of repeating disaccharide units will be a function of the species and age and the animal (e.g., animal cartilage has been found to have longer such chains, especially of keratan sulfate, with increasing developmental age). Since a broad spectrum of molecular weights are suitable, the size distribution may also be either narrow or broad. Exemplary heteropolysaccarides have molecular weights in the 5,000 to 5,000,000 range, and especially 10,000 to 500,000 although the invention is not limited in this respect. The chondroitin sulfate A used in the examples had an average molecular of 50,000.

Many of the heteropolysaccharides useful in the invention ar already commercially available. For example, chondroitin sulfate A, chondroitin sulfate C and keratan sulfate, each believed to be derived from animal cartilage, are available from Calbiochem Inc. of La Jolla, Calif.

The proportion of heteropolysaccharide to be used can be determined by routine experimentation, with the understanding that increasing amounts in the final aqueous medium can yield increasing hybridization rates, but that eventually either solubility limits or some increase in viscosity may be reached. As illustrated with chondroitin sulfate A, however, the amounts needed for a substantial increase in hybridization rate can be low enough to avoid viscosity or surface tension excesses, even in the most difficult geometry of a capillary gap environment used for in situ hybridization of tissue.

One illustrative reagent combination is an aqueous solution of the probe, and especially a probe labeled with biotin, bromodeoxyuridine or dinitrophenyl or with an enzyme, and the heteropolysaccharide. It will be appreciated, however, that the probe and heteropolysaccharide can also be packaged in separate reagents and that the heteropolysaccharide can, if separate, be in an aqueous prediluted, concentrated or even dry powder form.

The aqueous medium commonly contains salts or other solutes such as formamide. Other ingredients may include buffers (e.g., citrate and phosphate buffers) and macromolecules such as proteins (e.g., albumin) or nonspecific nucleic acids (e.g., sheared salmon sperm DNA). Such macromolecules are often used in assays wherein an aqueous solution containing the probe (the probe cocktail) contacts a solid phase on which the sample or a sample extract has been immobilized (a tissue section or the nucleic acid extracted from sample immobilized on nitrocellulose). Such macromolecules are used to reduce the non-specific binding of probe to the solid phase. At least some of the heteropolysaccharides used in the present invention may serve that function as well, blocking the sites for non-specific binding on the solid phase such as nitrocellulose.

An exemplary probe cocktail has the formulation:

| Ingredient | Range | Exemplary Amount |
|---|---|---|
| Chon. Sul. A | 0.5-10% | 2.5% |
| formamide | 10-60% | 45% |
| saline citrate | 2-8 × SSC | 5 × SSC |
| phosphate | 0.01-0.5M | 25 mM |
| herring DNA | 0-250 | 250 ug/ml |

The appropriate proportions of salts (e.g., sodium citrate, sodium diacid phosphate and disodium acid phosphate) are used to form a buffer of suitable pH (e.g. 7-8). The ingredients can be introduced in varous orders such as, sequentially:

| | |
|---|---|
| Deionized formamide | 22.5 ml |
| 20 × standard saline citrate | 11.50 ml |
| 500 mM phosphate buffer | 2.50 ml |
| distilled water | 12.50 ml |
| chondroitin sulfate A (Calbiochem) | 1.25 g |
| sheared herring sperm DNA | 12.5 mg. |

Hybridization rates are enhanced greatly at either 2.5%, 5% or 10% chondroitin sulfate A (the above formulation represents 2.5%). If the cocktail is to be heated to high temperatures (as to 110 deg C. for 10 minutes in the sample denaturing step of an in situ hybridization assay), the volume of water lost to evaporation decreases with increasing amounts of chondroitin sulfate A.

While macromolecules such as herring sperm DNA can be included, they have been found not to be necessary with the above exemplary formulation. Surfactants such as Brij 35 or Triton X-100 may also be present, especially if the cocktail is to be used for capillary gap applications. It is not necessary, however, for the surfactant to be in the probe cocktail with the heteropolysaccharide, since it will usually suffice that the surface (e.g., glass slide or nitrocellulose layer) has been contacted with a solution containing the surfactant prior to introduction of the probe cocktail into the gap (see Unger et al. "Automation Of in situ Hybridizaton." J. Histotechnology vol. 11, no. 4 pp. 253-58 (1988) and copending, commonly-assigned application U.S. Ser. No. 253,134 of Brigati, filed Oct. 4, 1988).

Illustrative of the various microscopic geometries in which the present invention can be practised are:
In situ hybridizations—see Unger et al article
Probe cocktail contacting sample extract on nitro-cellulose filter—see U.S. Ser .No. 253,134
Sandwich assays—see U.S. Pat. Nos. 4,486,539 and 4,564,597 to Ranki et al and 4,751,177 to Stabinsky
Displacement assays—see U.S. Pat. Nos. 4,818,680 Collins et al, 4,766,062 to Diamond et al and 4,752,566 to Collins et al
Solution hybridizations—see PCT WO 84/02721 of Kohne et al.

Illustrative of the various macroscopic environments in which the present invention can be practised are:
Capillary gap methodologies of U.S. Pat. Nos. 4,731,335, 4,777,020, 4,798,706 and 4,801,431 as well as U.S. Ser. No. 253,134;
Packed column environments of C.P.H. Vary et al, "Nonisotopic detection methods for strand displacement assays, Clin. Chem. vol. 32, pp. 1696 - (1986), and
Filter paper surface environments of J. H. Lin et. al. *J. of Virological Methods*, vol. 15, pp. 139-149 (1987).

EXAMPLES

The following examples were performed using the CODE-ON automated stainer (Fisher Scientific Company) following the general capillary gap methodology of U.S. Pat. No. 4,731,335. Further details are contained in various articles such as K. T. Montone et al., "Anatomic Viral Detection Is Automated," *Yale J of Biol. & Med.*, vol. 62, pp. 141-158 (1989) and in references 6 and 7 thereof. The stations (see FIG. 6 of U.S. Pat. No. 4,731,335 and FIG. 2 of Montone et al) were set up as follows:

1. Aqueous hematoxylin (Biomeda).
2. Distilled water/BRIJ 35
3. 95% Ethanol
4. Methanol/3% aqueous hydrogen peroxide
5. Reagent alcohol (100% ethanol)
6. Hemo-De clearing agent (a limoline-based product)
7. Probe wash (2×SSC)
8. Blotter
9. Blotter
10. Automation buffer (Biomeda, 1×)
11. Blotter
12. Blotter
13. Enzyme (pepsin at 0.2 mg/ml in 0.12N aqueous HCl with 2.5 ul of 30% BRIJ 35 per ml)
14. Probe cocktail (see above formulation containing chondroitin sulfate A)
15. Detection system (avidin conjugated alkaline phosphatase, from DAKO of Carpentiera, Calif.)
16. Chromagen (BCIP/INT)
17. Not used
18. Incubation chamber
19. High temperature oven
0. Cool down chamber.

The detection system in station 15 was made up by diluting avidin-alkaline phosphatase 1:200 in 1X automation buffer (Biomeda) with 0.1% BSA, 1 mg/ml sodium aide and 3 uM magnesium chloride. The chromagen in station 16 was made up by adding 200 ul of a 25 mg/ml solution of p-iodonitrotetrazolium violet (INT) in a 50/50 solution of dimethylformamide and distilled water, and 100 ul of a 50 mg/ml solution of 5-bromo-4-chloro-3-indoyl phosphate p-toliudine salt (BCIP) in dimethylformamide to 30 ml of Tris saline, pH 9.5.

The robotic sequence is summarized in the following Table (similar to Table 2 of the Montone et al article):

| Event | Station | Time | Temp | Solution |
|---|---|---|---|---|
| 01 | 06 | 0.3 | | Clear (Hemo-De) |
| 02 | 19 | 10.0 | 90 C. | Denaturing oven |
| 03 | 12 | 0.3 | | Pad (blotter) |
| 04 | 06 | 0.1 | | Clear |
| 05 | 19 | 0.2 | 90 C. | Denaturing oven |
| 06 | 12 | 0.1 | | Pad |
| 07 | 06 | 0.1 | | Clear |
| 08 | 12 | 0.3 | | Pad |
| These steps clear the wax from the specimen | | | | |
| 09 | 05 | 0.1 | | Reagent alcohol |
| 10 | 12 | 0.2 | | Pad |
| 11 | 05 | 0.1 | | Reagent alcohol |
| 12 | 12 | 0.2 | | Pad |
| 13 | 05 | 0.1 | | Reagent alcohol |
| 14 | 12 | 0.5 | | Pad |
| 15 | 13 | 0.5 | | Enzyme (pepsin) |
| 16 | 18 | 10 | 40 C. | Chamber |
| 17 | 11 | 0.6 | | Pad |
| 18 | 10 | 0.1 | | Buffer |

These steps extract the clearing agent and digest proteins to expose the nucleic acids in the sample

| | | | | |
|---|---|---|---|---|
| 19 | 11 | 0.6 | | Pad |
| 20 | 03 | 0.3 | | 95% alcohol |
| 21 | 11 | 0.6 | | Pad |
| 22 | 05 | 0.3 | | Reagent alcohol |
| 23 | 11 | 0.6 | | Pad |
| 24 | 05 | 0.1 | | Reagent alcohol |
| 25 | 11 | 0.5 | | Pad |

These steps wash out and inactivate the pepsin

| | | | | |
|---|---|---|---|---|
| 26 | 14 | 1.0 | | Probe cocktail |
| 27 | 19 | 8.0 | 100 C. | Denaturing oven |
| 28 | 00 | 3.0 | | Cool down chamber |
| 29 | 18 | 60.0 | 40 C. | Incubation chamber |

These steps apply the probe, melt double-stranded nucleic acids and then permit rehybridization of probe to target sequences

| | | | | |
|---|---|---|---|---|
| 30 | 07 | 0.5 | | Probe wash |
| 31 | 09 | 0.1 | | Pad |
| 32 | 07 | 5.0 | | Probe wash |
| 33 | 09 | 0.6 | | Pad |
| 34 | 07 | 3.0 | | Probe wash |
| 35 | 09 | 0.6 | | Pad |
| 36 | 07 | 3.0 | | Probe wash |
| 37 | 09 | 0.6 | | Pad |

These steps removed unhybridized probe from the sample; the probe wash has 2X SSC

| | | | | |
|---|---|---|---|---|
| 38 | 15 | 0.6 | | Detection system (Av-AP) |
| 39 | 18 | 20 | 40 C. | Incubation chamber |
| 40 | 09 | 0.2 | | Pad |
| 41 | 10 | 0.1 | | Buffer |

| | | | | |
|---|---|---|---|---|
| 42 | 11 | 0.6 | | Pad |

These steps attach avidin-enzyme to biotin on probe

| | | | | |
|---|---|---|---|---|
| 43 | 16 | 0.2 | | Chromagen (BCIP/INT) |
| 44 | 09 | 0.6 | | Pad |
| 45 | 16 | 0.5 | | Chromagen |
| 46 | 18 | 7.0 | 45 C | Incubation chamber |
| 47 | 09 | 0.6 | | Pad |
| 48 | 16 | 0.5 | | Chromagen |
| 49 | 18 | 15.0 | 45 C | Incubation chamber |
| 50 | 09 | 0.6 | | Pad |

These steps develop color where the enzyme is attached on the sample

| | | | |
|---|---|---|---|
| 51 | 01 | 0.1 | Hematoxylin |
| 52 | 09 | 0.6 | Pad |
| 53 | 07 | 0.1 | Probe wash |
| 54 | 09 | 0.6 | Pad |
| 55 | 07 | 0.6 | Buffer |
| 56 | 10 | 0.6 | Pad |

These steps counterstain the cell nuclei.

Following this procedure, the slides were removed from the slideholder, air dried and coverslipped with Crystal Mount (biomeda).

EXAMPLE 1

The above protocol was used wherein the probe coctail contained one or both of the following oligonucleotides, chemically labeled with 3-4 biotin molecules per probe at the 3' termini:

Alu 1 5'-TGT AATCCCAGCACT T TGGGAGGCT-3'
Alu 2 5'-CT GCACTCCAGCT GGGC-3'

Excellent staining of the DNA of human cell nuclei resulted when either of the Alu 1 and Alu 2 probes were present at 60 ng/ml (or each was present at 30 ng/ml) of the probe coctail described above (with 10% chondroitin sulfate A). With that level of chondroitin sulfate A, the time (at event 27) in the denaturing oven can be extended to as much as ten minutes.

EXAMPLE 2

When example 1 was repeated using probe cocktails having 2.5% or 5.0% chondroitin sulfate, similar results were obtained. Using more that 60 ng/ml of oligonucleotide probes sometimes resulted in increased background staining.

COMPARATIVE EXAMPLE 3

For comparison, a commercially available probe cocktail (from AMRESCO) having 45% formamide and 10% dextran sulfate was used. In this example, the washing of the probe from the slides (events 30-37) was incomplete unless a step of 3 to 5 minutes at 45 degrees C. (in the incubator of station 18) was inserted after event 30, 32 and 34.

EXAMPLE 4

The procedures of Example 1 were followed (with chondroitin sulfate at 2.5% in the probe cocktail used in station 14). A chemically biotin-labeled 23-mer oligonucleotide probes of the following sequence (taken from the Not 1/Pst I region of Epstein-Barr virus) was used at a level of 60 ng/ml:

5'-TGGGCCGCTGCCCCGCTCCGGGT-multi biotin labelled 3'amine.

Slides of uninfected normal splenic tissue showed little background staining. Slides from the formalin-fixed, paraffin embedded lymphocytes from the spleen of a patient diagnosed as having died from a disseminated EBV infection showed excellent staining by this probe, developed as indicated above with Av-AP and BCIP/INT. The large, atypical lymphocytes were consistently stained by this procedure. Uninfected cells were not stained. The lymphocytes of a CMV infected patient were not stained by the probe cocktail using this procedure.

EXAMPLE 5

The procedures of Example 1 were followed (with chondroitin sulfate at 2.5% in the probe cocktail used in station 14), except that event 1-8 were omitted since the cells being tested were not paraffin embedded. Commercially available biotinylated probes (Enzo Corporation) against EBV, cytomegalovirus (CMV) or herpes simplex virus (HSV) were used according to the manufacturer's suggested concentration and diluted in the chondroitin sulfate cocktail. Cocktails containing the EBV probe stained EBV-infected cells from tissue culture. Cocktails containing the CMV probe stained CMV-infected cells from tissue culture. Cocktails containing the HSV probe stained HSV-infected cells from tissue culture. No cross-reactivity was observed between the EBV probe and the CMV-infected cells and between the CMV probe and the EBV-infected cells.

What is claimed is:

1. A method for increasing the rate of hybridization between two complementary polynucleotide segments in an aqueous medium which comprises the step of forming an aqueous medium containing the two complementary polynucleotide segments and a water-soluble heteropolysaccharide having an alternating structure of sulfated N-acetylgalactosamine and an unsulfated monosaccharide, the water-soluble heteropolysaccharide being of sufficient molecular weight and concentration to produce an observable increase in the rate of hybridization.

2. The method of claim 1 wherein the unsulfated monsaccharide is D-glucuronic acid.

3. The method of claim 2 wherein the water-soluble heteropolysaccharide is chondroitin sulfate C.

4. The method of claim 2 wherein the water-soluble heteropolysaccharide is chondroitin sulfate A.

5. The method of claim 4 wherein the chondroitin sulfate A is of an average molecular weight of 5,000 to 500,000.

6. The method of claim 4 wherein one of the complementary polynucleotide segments is provided in a probe cocktail at a concentration of 1 to 1000 ng/ml and the other of the complementary polynucleotide segments is contained within an immobilized sample.

7. The method of claim 6 wherein chondroitin sulfate A is present in the probe cocktail at a concentration of 1-15%.

8. A reagent system for determining a particular polynucleotide segment in a test sample, comprising in the same or different containers in a packaged combination:

a) a polynucleotide probe having a base sequence substantially complementary to the sequence to be determined, and b) a water-soluble heteropolysaccharide having an alternating structure of sulfated N-acetylgalactosamine and an unsulfated monosaccharide, the water-soluble heteropolysaccharide being of sufficient molecular weight and amount to produce an observable increase in the rate of hybridization when the polynucleotide probe and water-soluble heteropolysaccharide are combined with a sample in an aqueous medium.

9. The reagent system of claim 8 wherein the unsulfated monsaccharide is D-glucuronic acid.

10. The reagent system of claim 9 wherein the water-soluble heteropolysaccharide is chondroitin sulfate C.

11. The reagent system of claim 9 wherein the water-soluble heteropolysaccharide is chondroitin sulfate A.

12. The reagent system of claim 11 wherein the chondroitin sulfate A is of an average molecular weight of 5,000 to 500,000.

13. The reagent system of claim 12 whererein the polynucleotide probe is at a concentration of 1 to 1000 ng/ml.

14. The reagent system of claim 12 wherein chondroitin sulfate A is present at a concentration of 1-15%.

* * * * *